United States Patent [19]

Porat et al.

[11] E Patent Number: Re. 32,974

[45] Reissued Date of Patent: Jul. 4, 1989

[54] SYRINGE

[76] Inventors: Michael Porat; Amir Porat, both of 4 Hirschenberg Street; Doron Lachish, 11 Ester Hamalka Street, all of Tel-Aviv, Israel

[21] Appl. No.: 108,768

[22] Filed: Oct. 15, 1987

Related U.S. Patent Documents

Reissue of:

[64] Patent No.: 4,583,978
Issued: Apr. 22, 1986
Appl. No.: 571,192
Filed: Jan. 16, 1984

[51] Int. Cl.[4] ..... A61M 5/00

[52] U.S. Cl. ..... 604/208; 604/218

[58] Field of Search ..... 604/208, 207, 211, 239, 604/181-191

[56] References Cited

U.S. PATENT DOCUMENTS

| | | | |
|---|---|---|---|
| 984,037 | 2/1911 | Sheets | 604/191 |
| 1,707,880 | 4/1929 | Sheets | 604/191 X |
| 2,515,956 | 7/1950 | Greenberg . | |
| 2,561,273 | 7/1951 | Hamilton | 604/191 X |
| 2,646,042 | 7/1953 | Hu | 604/191 X |
| 3,232,117 | 1/1966 | Gilmont | 604/211 |
| 3,327,904 | 6/1967 | Goda | 222/309 |
| 3,749,084 | 7/1973 | Cucchiara | 604/239 |
| 3,754,687 | 7/1973 | Norton | 604/211 |
| 3,815,785 | 6/1974 | Gilmont . | |
| 3,960,139 | 6/1976 | Bailey | 604/218 X |
| 4,153,056 | 5/1979 | Silver et al. | 604/211 |
| 4,261,359 | 4/1981 | Chein . | |
| 4,313,440 | 2/1982 | Ashley | 604/239 |

FOREIGN PATENT DOCUMENTS

| | | | |
|---|---|---|---|
| 0058536 | 8/1982 | European Pat. Off. | 604/218 X |
| 167058 | 5/1904 | Fed. Rep. of Germany . | |
| 516791 | 1/1931 | Fed. Rep. of Germany . | |
| 1216753 | 4/1960 | France . | |
| 510484 | 8/1939 | United Kingdom . | |

*Primary Examiner*—John D. Yasko
*Attorney, Agent, or Firm*—Dennison, Meserole, Pollack & Scheiner

[57] ABSTRACT

A syringe system for storing medication and dispensing dosed quantities thereof, including a housing, a storage chamber in the housing, a dose chamber in the housing and in direct communication with the storage chamber, a first piston for introducing a fluid into the storage chamber and subsequently for introducing by pressure a predetermined volume of the fluid into the dose chamber, and a second piston for expelling the volume of fluid from the dose chamber and from the housing.

3 Claims, 2 Drawing Sheets

SYRINGE

Matter enclosed in heavy brackets [ ] appears in the original patent but forms no part of this reissue specification; matter printed in italics indicates the additions made by reissue.

*This application is a reissue of Ser. No. 571,192 filed Jan. 16, 1984 now U.S. Pat. No. 4,583,978.*

The present invention concerns a syringe in which a predetermined quantity of medication can be stored to be dispensed in predetermined doses as required. In medicine, for example for diabetic patients, or in dentistry, for example for aneasthetic purposes, individual disposable syringes are provided, each being used for one dose of the injection required. It is clear that this is wasteful and costly procedure, particularly since in most cases the same quantity of medication is required for each injection. Furthermore, it is often desirable that the physician fills a syringe with the quantity of medication sufficient for the entire course of treatment and adjusts the syringe so that the patient, upon each actuation of the syringe will always inject only the required dose.

It is the purpose of the present invention to provide a syringe which is adapted to store a quantity of medication for multiple injections and with which predetermined doses of this medication can be expelled.

The present invention consists in a syringe for storing medication and dispensing dosed quantities thereof, constituted by a housing and two piston-like devices, the filling operation of the entire quantity of the medication being effected by one device under vacuum, while the filling of the dosed quantity to be injected is effected by the other device under pressure.

Figure 1:
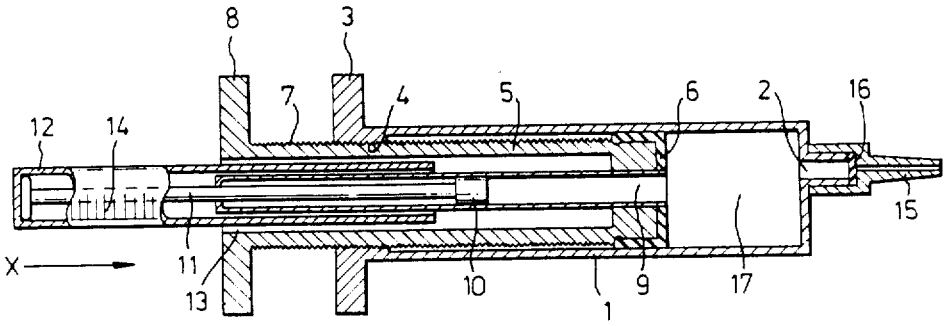
Figure 2:
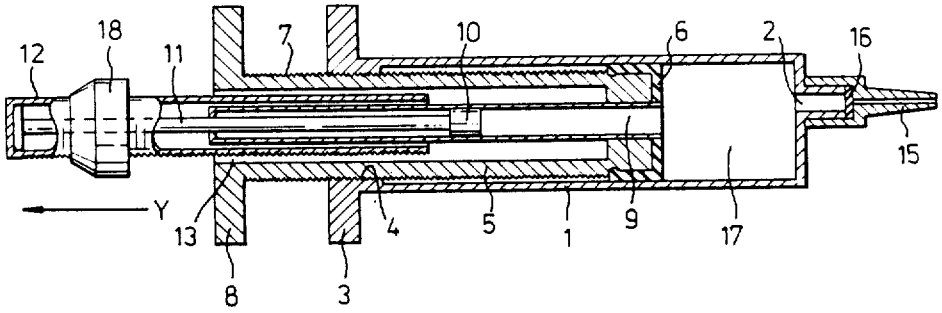
Figure 3:
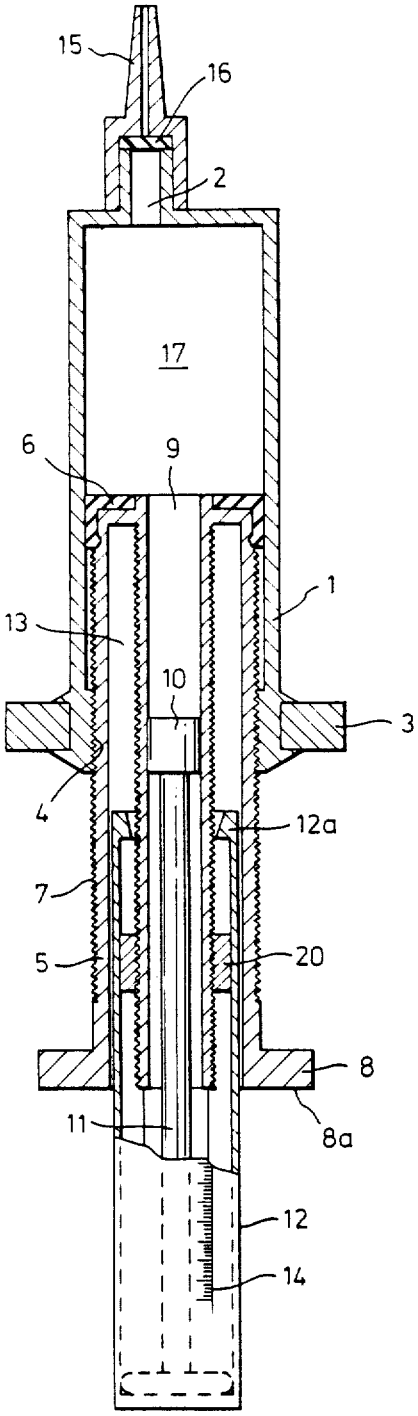

The invention is illustrated by way of example only in which:

FIGS. 1, 2 and 3 show longitudinal schematic sections of three embodiments of the syringe according to the invention, the embodiment of FIG. 3 being shown on a large scale.

Figure 3A:
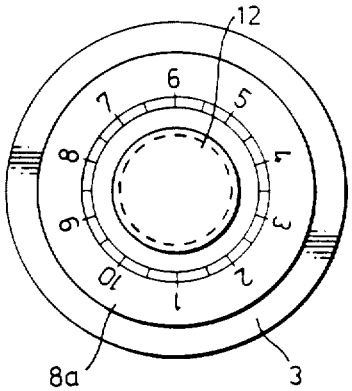

FIG. 3*a* shows the radial calibration provided on the embodiment of FIG. 3.

As shown in FIG. 1 an outer syringe housing is provided with an outlet opening 2 at the closed end and a circumferential flange 3 at the open end, a short internal thread 4 being provided at this end. A cylindrical casing 5, having an external thread 7 along its length, is rotatably movable within housing 1, its inner end 6 constituting a piston. At the end opposite to end 6 a circumferential flange 8 is provided. Casing 5 has an axially extending cylindrical sleeve defining a dose chamber 9 which merges with end 6 and in which a piston 10 is longitudinally movable by its rod 11. Said rod is covered by a tubular handle 12, which extends into an annular well 13 in casing 5 surrounding sleeve 9 and is adapted to engage the rod 11 in a manner so that it can be moved therewith. Tube 12 is linearly calibrated at 14 as shown.

The syringe works as follows:

A two way hypodermic needle (not shown) which is double-sided, is attached in the conventional manner to a cap 15 which covers the end of outlet opening 2 with the interposition of an elastic washer 16, the needle penetrating said washer. By rotating casing 5 relative to housing 1, the space 17 therein between its ends and the end 6 will be filled. The space 17 defines a storage chamber. Now the said needle is withdrawn. The filling process of space or dose chamber 9 is continued by rotating casing 5 towards opening 2 whereby owing to the pressure within space or storage chamber 17, piston 10 together with handle 12 will move in a direction opposite to that of arrow X and fill sleeve dose chamber 9 also until the calibration 14 indicates a certain predetermined dose. Now in order to dispense said predetermined dose a second hypodermic needle which is a finer one is attached and penetrates washer 16 in order to inject a smaller, but predetermined dose. This is effected by pushing handle 12 in the direction of arrow X, a stop (not shown) preventing this movement after the end of piston 10 has reached the end 6 of casing 5. After the needle is removed, piston 10 will remain in its position until a further injection is made. At this time casing 5 will be screwed into housing 1 up to the point where the proper calibration 14 will be shown again and this will force piston 10 into the direction opposite to the arrow thereby filling sleeve dose chamber 9 with the proper dose.

In the embodiment of the syringe shown in FIG. 2 the parts which have the same reference numerals as those in FIG. 1 are the same and operate similarly and will not be further described. The additional part in this case is a threaded ring 18 which is screwed into threaded and calibrated handle 12 to serve for fixing a predetermined fixed dose. This syringe works as follows:

The filling of chambers 17 and 9 is carried out in the same way as that of FIG. 1, the difference being that the movement of the piston 10 and handle 12 in the direction of arrow Y is continued until the piston 10 reaches a stop in casing 5. Thus the entire dose chamber 9 is filled. Ring 18 is now rotated on handle 12 up to the calibration which indicates the required dose and when the injection is to take place handle 12 is pushed to the right in a direction opposite to that of arrow Y until ring 18 meets flange 8 whereby dose chamber 9 will be emptied by a quantity corresponding to the required dose.

In the embodiment of the syringe of FIG. 3 the parts which are the same or similar to those of FIGS. 1 and 2 will not be particularly described. The syringe differs from those described with respect ot FIGS. 1 and 2 in that it can be used for fixed dosing with the use of a different way of calibration. For this purpose the tubular handle 12 has a hexagonal internal cross-section, a hexagonal nut 20 being housed in its inner end and being held therein by an internal flange 12*a*, thus that handle 12 can freely move axially and when rotated, will force nut 20 to rotate. The tubular wall of sleeve dose chamber 9 is provided with an external thread along its length adapted to be screwingly engaged by nut 20. The circumferential flange 8 is provided with radial calibrations 8*a*, ten being shown here, the relationship between calibration 14 and calibration 8*a* being similar to that used in a micrometer.

The filling of space dose chamber 17 is carried out in the same way as that of FIG. 1. When now an accurate dose is to be dispensed, handle 12 is rotated taking nut 20 with it until the desired calibration 14 appears against flange 8. Now casing 5 is rotated whereby dose chamber 9 is filled as above, the piston 10 being stopped in its movement when flange 12*a* meets nut 20, whereby a predetermined fixed dose will be filled in dose chamber 9. The next dosage will now be exactly that of the first one. Since the calibration 14 may be difficult to read, calibration 8*a* will show a more accurate reading.

The profile of the internal wall of handle 12 may have any other shape than that described, e.g. square or any other geometric shape, or a circular nut may be provided with diametrically opposed lugs which engage in diametrically opposed elongated slits in the wall of handle 12.

The calibrations may be raised, so that the syringe can be used by the blind.

We claim:

[1. A syringe for storing medication and dispensing dosed quantities thereof, comprising a housing, a storage chamber in said housing, a dose chamber in said housing and in direct communication with said storage chamber, first piston means for introducing a fluid into said storage chamber and subsequently for introducing by pressure a predetermined volume of the fluid into said dose chamber, second piston means for expelling the volume of fluid from the dose chamber and from the housing, and means for preventing relative movement between said first piston means and said housing when said second piston means expels fluid from the dose chamber.]

[2. The syringe of claim 1 wherein said first piston means is in direct communication with the storage chamber and operable to vary the volume thereof for a selective increase in the volume to permit the inflow of fluid therein, and for a selective reduction in the volume for generating an increase of pressure therein and an outflow of fluid into said dose chamber.]

[3. The syringe of claim 1 wherein said second piston means is in direct communication with said dose chamber and mounted for outward movement relative thereto in response to increase in the volume of fluid in said dose chamber and for manual inward movement.]

[4. The syringe of claim 3 including means associated with said second piston means for indicating the volume of fluid in said dose chamber.]

[5. A syringe for storing medication and dispensing dosed quantities thereof, comprising a housing, a storage chamber in said housing, a dose chamber in said housing and in direct communication with said storage chamber, first piston means for introducing a fluid into said storage chamber and subsequently for introducing by pressure a predetermined volume of the fluid into said dose chamber, and second piston means for expelling the volume of fluid from the dose chamber and from the housing, said first piston means being in direct communication with the storage chamber and operable to vary the volume thereof for a selective increase in the volume to permit the inflow of fluid therein, and for a selective reduction in the volume for generating an increase of pressure therein, said second piston means being in direct communication with said dose chamber and mounted both for outward movement in response to increase in the volume of fluid in said dose chamber and for manual inward movement, means associated with said second piston means for indicating the volume of fluid in said dose chamber, said first and second piston means being coaxial, said first piston means having an inner end and an outer end, said dose chamber opening axially through said inner end, said second piston means including an inner end and an outer end, said second piston means extending axially through said first piston means with the inner end of the second piston means in said dose chamber and the outer end of the second piston means at the outer end of said first piston means.]

[6. The syringe of claim 5 wherein said means for preventing relative movement between said first piston and said housing includes engaged screw thread means on and between said first piston means and said housing whereby rotational movement of said first piston means relative to said housing will effect a longitudinal movement of said first piston means relative to said housing and the storage chamber therein.]

[7. The syringe of claim 5 wherein the means for indicating the volume of fluid in said dose chamber comprises a tubular handle received over said second piston means, said tubular handle having calibrations thereon.]

[8. The syringe of claim 7 including means on said handle to adjustably limit inward movement of said second piston means.]

9. [The syringe of claim 8 wherein] *A syringe for storing medication and dispensing dosed quantities thereof comprising:*

*a housing;*

*a storage chamber within said housing and defining an outlet opening therein;*

*a dose chamber in said housing in direct communication with said storage chamber;*

*first piston means partially within said housing for initially introducing a fluid into said storage chamber through said outlet opening and subsequently for introducing by pressure a predetermined volume of the fluid into said dose chamber; and*

*second piston means partially within said first piston means for expelling the volume of fluid from the dose chamber;*

*said first piston means being in direct communication with the storage chamber and operable to vary the volume thereof for a selective increase in the volume to permit the inflow of fluid therein, and for a selective reduction in the volume for generating an increase of pressure therein;*

*said second piston means being in direct communication with said dose chamber and operable to vary the volume thereof and mounted for outward movement in response to an increase in the volume of fluid in said dose chamber and for manual inward movement;*

*means associated with said second piston means for indicating the volume of fluid in said dose chamber;*

*said first and second piston means being coaxial, said first piston means having an inner end and an outer end, said second piston means extending axially through said first piston means with the inner end of the second piston means in said dose chamber and the outer end of the second piston means at the outer end of said first piston means;*

*means for preventing relative movement between said first piston means and said housing when said second piston means is moved to expel fluid from the dose chamber;*

*sealing means mounted adjacent the outlet opening of said storage chamber and selectively openable to allow fluid movement therethrough;*

*said means for preventing relative movement comprising engaged screw thread means on and between said first piston means and said housing arranged such that rotational movement of said first piston means relative to said housing will effect a longitudinal movement of said first piston means relative to said housing and the storage chamber therein;*

*said means for indicating the volume of fluid in said dose chamber comprising a tubular handle received over said second piston means and having calibrations thereon;*

*means on said handle to adjustably limit outward movement of said second piston means; and* said dose chamber [is ] *being* defined by an alongate sleeve opening through the inner end of said first piston means, said second piston means being received in said sleeve, said means to adjustably limit inward movement of said second piston means comprising a nut means adjustably mounted on said sleeve, said handle being longitudinally slidable over said nut means, and abutment means on said handle engageable with the nut means, as adjusted, to limit outward movement of said handle and said second piston means.

[10. The syringe of claim 6 including a flange on and surrounding said first piston means, said flange including radial calibrations thereon.]

[11. A syringe for storing medication and dispensing dosed quantities thereof, comprising a housing defining an interior storage chamber, an outlet in said housing communicating with said storage chamber and selectively openable to allow fluid movement therethrough, first piston means within said housing, said first piston means being operable exteriorly of said housing for selective outward movement relative to said housing to increase the volume of said storage chamber, said storage chamber other than for said outlet, being hermetically sealed, a hermetically sealed dose chamber communicating with said storage chamber remote from said outlet, second piston means operable within said dose chamber in response to pressure variation therein, said second piston means being exteriorly accessible whereby a pressure increase in said dose chamber will effect an outward movement of said second piston means and a corresponding increase in the volume of said dose chamber, said first piston means being operable for selective inward movement for reducing the interior volume of the sealed storage chamber and for effecting a pressure increase in said storage chamber and the communicating dose chamber in conjunction with a movement of fluid from said storage chamber into said dose chamber, said second piston means being outwardly movable relative to said dose chamber in response to movement of fluid into said dose chamber, means for indicating the amount of fluid introduced into said dose chamber by a fluid-moving pressure increase effected by an inward movement of said first piston means, said second piston means, upon an opening of said outlet, being inwardly movable relative to the dose chamber to reduce the volume therein, expel the fluid therefrom and discharge an equivalent volume of fluid through said outlet, and means for preventing relative movement between said first piston means and said housing when said second piston means expels fluid from the dose chamber.]

[12. A method of storing and selectively dispensing doses of medication utilizing a syringe including a storage chamber with a first piston means for selectively varying the volume of and pressure within the storge chamber, a dose chamber in direct communication with the storage chamber, second piston means for selectively varying the volume of and pressure within the dose chamber, and means for preventing relative movement between said first piston means and said storage chamber when said second piston means expels fluid from said dose chamber; said method including the steps of communicating said storage chamber with a source of medication, reducing the pressure within said storage chamber and inducing an inward flow of the medication, closing the communication with the source of medication, increasing the pressure in the storage chamber and inducing a flow of medication from the storage chamber into the dose chamber through manipulation of said first piston means, positioning the first piston means in a fixed position relative to said storage chamber, communicating said storage chamber with a receiver of said medication, increasing pressure within said dose chamber and inducing a predetermined flow of medication from said dose chamber into said storage chamber and from said storage chamber to a receiver while maintaining the first piston means in the fixed position.]

[13. The method of claim 12 wherein said first piston means is in direct communication with said storage chamber, said second piston means being in direct communication with said dose chamber, the step of reducing pressure in said storage chamber and inducing inward flow including a retraction of said first piston means relative to said storage chamber, the step of increasing pressure in the storage chamber and inducing flow into the dose chamber including an extension of said first piston means inwardly of said storage chamber, and the step of increasing pressure within said dose chamber and inducing flow from said dose chamber including an extension of said second piston means inward of said dose chamber.]

*14. A syringe as claimed in claim 9 wherein said sealing means comprises an elastic washer which can be penetrated by a hypodermic needle.*

*15. A syringe as claimed in claim 9 or claim 14, wherein radial calibrations are provided on a flange on and surrounding said first piston means.*

* * * * *